(12) United States Patent
Miano et al.

(10) Patent No.: US 7,404,279 B1
(45) Date of Patent: *Jul. 29, 2008

(54) SILVERWARE AND NAPKIN ROLLING APPARATUS

(76) Inventors: Mario L. Miano, 731 Sitka St., Fort Collins, CO (US) 80524; Kevin W. Nelson, 1401 Sugarpine St., Fort Collins, CO (US) 80524

( * ) Notice: Subject to any disclaimer, the term of this patent is extended or adjusted under 35 U.S.C. 154(b) by 0 days.

This patent is subject to a terminal disclaimer.

(21) Appl. No.: 11/240,957

(22) Filed: Oct. 3, 2005

Related U.S. Application Data

(63) Continuation-in-part of application No. 10/968,779, filed on Oct. 20, 2004, now Pat. No. 6,976,348, which is a continuation-in-part of application No. 10/641,357, filed on Aug. 15, 2003, now Pat. No. 6,837,028.

(60) Provisional application No. 60/407,574, filed on Sep. 3, 2002.

(51) Int. Cl.
   *B65B 21/06* (2006.01)
(52) U.S. Cl. ............... 53/443; 53/229; 53/415; 53/466
(58) Field of Classification Search ............ 53/206, 53/209, 222, 228, 229, 415, 443, 466, 155, 53/586, 588
   See application file for complete search history.

(56) References Cited

U.S. PATENT DOCUMENTS

| 3,571,939 A * | 3/1971 | Paul .................. 34/275 |
| 6,918,226 B2 * | 7/2005 | Heilman et al. ........ 53/211 |
| 2002/0112445 A1 * | 8/2002 | Scaduto .............. 53/167 |
| 2002/0122743 A1 * | 9/2002 | Huang ................ 422/24 |
| 2003/0150475 A1 * | 8/2003 | Abrams et al. ......... 134/1 |

\* cited by examiner

*Primary Examiner*—Hemant M. Desai
(74) *Attorney, Agent, or Firm*—John D. Gugliotta, PE, Esq

(57) ABSTRACT

An apparatus that wraps dinner flatware in a paper napkin in an automated manner and secures it with a paper label is disclosed. The apparatus includes input hoppers for knives, forks, spoons, and napkins which are located on the front and top part of the unit. Additionally, a roll of paper napkins and a roll of securing paper labels are provided on top with their own automatic dispensing means. A plastic cover secures the entire top of the invention to protect it from dust and dirt as well as accidental contact during operation. A series of ultraviolet radiation sources reduces and/or eliminates microbes and viruses either on the surface of the flatware or airborne inside the apparatus. Internal mechanisms then take one of each piece of flatware and fold and roll it in a napkin. The completed napkin unit then drops out the bottom where it is collected for use.

10 Claims, 5 Drawing Sheets

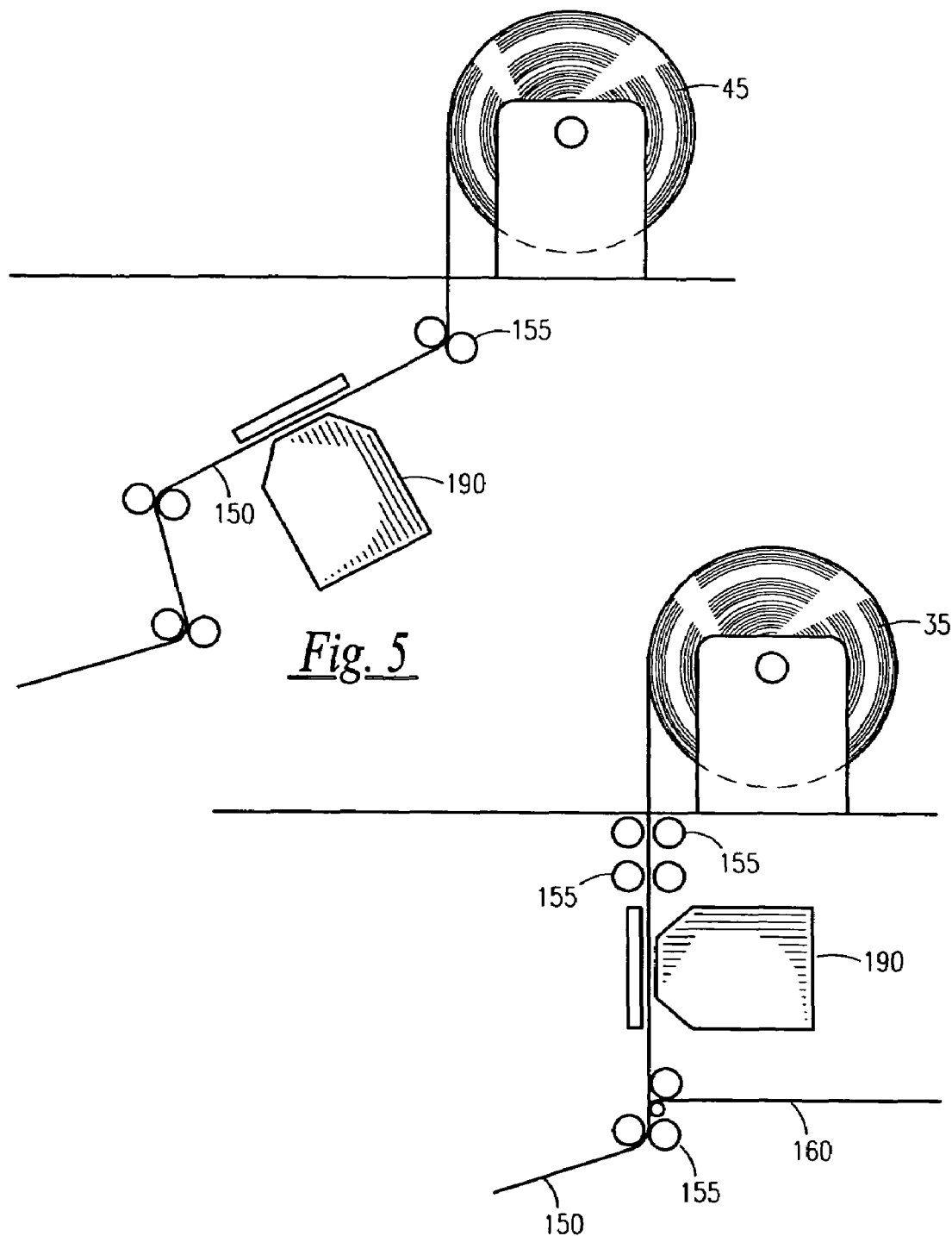

SILVERWARE AND NAPKIN ROLLING APPARATUS

RELATED APPLICATIONS

The present invention is a Continuation in Part of U.S. Ser. No. 10/968,779, filed on Oct. 20, 2004, now U.S. Pat. No. 6,976,348 issued on Dec. 20, 2005, which was a Continuation in Part of U.S. Ser. No. 10/641,357, filed on Aug. 15, 2003, now U.S. Pat. No. 6,837,028 issued on Jan. 4, 2005, which claimed the benefit of U.S. Provisional Patent 60/407,574 filed on Sep. 3, 2002.

BACKGROUND OF THE INVENTION

1. Field of the Invention

The present invention relates generally to automated assembling apparatuses and, more particularly, to an automated flatware and napkin assembling apparatus.

2. Description of the Related Art

In many restaurants, silverware or flatware, is folded or rolled up in a paper napkin and secured with an adhesive paper strap. This has many advantages from increased sanitary conditions, less chance of falling on the floor, a more professional presentation and so forth. This presentation technique is also finding favor in cafeteria environments where bins of flatware were often used before. These previously used bins forced patrons to touch more flatware than was necessary to remove just one piece, resulting in more unsanitary conditions, especially in environments such as schools and hospitals. However, the practice of rolling flatware in a napkin is not without its disadvantages. Perhaps the biggest is the cost of paying a restaurant or cafeteria employee to roll them. Even if an employee is efficient at such a task, he or she will almost certainly produce non-consistent rolled napkins thus reducing that professional image. Accordingly, a need exists for a means by which silverware or flatware can be folded in a paper napkin without the disadvantages of the folding methods that are currently used.

A search of the prior art did not disclose any patents that read directly on the claims of the instant invention; however, the following references were considered related.

Accordingly, a need exists for a means by which silverware/flatware can be rolled up into a napkin without the disadvantages of the methods that are currently used.

SUMMARY OF THE INVENTION

It is therefore an object of the present invention to provide an improved napkin rolling apparatus.

It is a feature of the present invention to provide an improved apparatus that wraps silverware/flatware (the terms silverware and flatware are synonymous herein) into a napkin and fastens the roll with an optional paper band that is plain or printed with any name, logo or advertising message. Briefly described according to one embodiment of the present invention, the silverware and napkin rolling apparatus, is an apparatus that wraps silverware/flatware (the terms silverware and flatware are synonymous herein) into a napkin and fastens the roll with a paper band. The silverware and napkin rolling apparatus has input hoppers for knives, forks and/or spoons and has input feed slots for napkins and paper containment bands. Additionally, as the silverware/flatware are wrapped, they are exposed to ultraviolet radiation thus killing and/or eradicating any remaining germs and bacteria.

The apparatus has a cover to protect users from physical injury when the apparatus is in operation and to protect the loaded silverware and napkins from dust and debris when not in operation, as well as protect the user from exposure to ultraviolet radiation during operation of the apparatus. Internal mechanisms work to transfer one knife, one fork and if desired one spoon to a trough where they meet with the napkin that is caused to cover the silverware.

A paper band is also passed through the machine and is forced around the napkin-silverware combination. If used, the paper band is caused to be sealed and the rolled silverware is then dispensed through the discharge chute and collected in an output tray.

The output tray is capable of holding up to fifty completed sets of rolled silverware.

The present invention is also equipped with sensors that halt operations when a necessary component is not available or when cover is opened during operation or when objects become lodged.

It is an object of the present invention to provide an apparatus that automatically wraps silverware into napkins.

It is another object of the present invention to provide an apparatus that quickly and conveniently wrap silverware in napkins.

It is yet another object of the present invention to sterilize silverware via ultraviolet radiation exposure to further aid in the elimination of microbiological bacterial contamination.

It is yet another object of the present invention to provide an apparatus that consistently results in near identical aesthetic wraps of silverware in napkins.

It is yet another object of present invention, which greatly reduces the amount of silverware having human contact thereby reducing the level of microbiological bacterial contamination.

It is yet another object of present invention which provides an institution an apparatus that quickly and conveniently wraps silverware into a napkin and continues to bind the rolled napkin with an optional plain or printed paper band.

| | DESCRIPTIVE KEY |
|---|---|
| 10 | automated flatware and napkin assembling apparatus |
| 15 | automation enclosure |
| 20 | start switch |
| 25 | stop switch |
| 30 | napkin reset switch |
| 35 | rolled paper napkins |
| 40 | label reset switch |
| 45 | rolled paper adhesive labels |
| 50 | mounting feet |
| 55 | spoon hopper |
| 60 | fork hopper |
| 65 | knife hopper |
| 70 | cover |
| 75 | limit switch |
| 80 | exit slot |
| 85 | power cord |
| 90 | power plug |
| 95 | spoon |
| 100 | fork |
| 105 | knife |
| 110 | first upper indexing plate |
| 115 | first lower indexing plate |
| 120 | sliding chute |
| 125 | first travel path |
| 130 | second travel path |
| 135 | second upper indexing plate |
| 140 | second lower indexing plate |
| 145 | third travel path |
| 150 | napkin stream |
| 155 | first indexing rollers |
| 160 | label stream |

-continued

| DESCRIPTIVE KEY | |
|---|---|
| 165 | second indexing rollers |
| 170 | flatware trough |
| 171 | first ultraviolet lamp tube |
| 172 | first ultraviolet lamp tube shield |
| 173 | second ultraviolet lamp tube |
| 174 | second ultraviolet lamp tube shield |
| 175 | fourth travel path |
| 180 | rotational travel path |
| 190 | ink jet printer head |

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 5 is a partial sectional view of the automated flatware and napkin assembling apparatus 10 according to a first alternate embodiment; and FIG. 6 is a sectional view of the automated flatware and napkin assembling apparatus 10 according to a second alternate embodiment.

DESCRIPTION OF THE PREFERRED EMBODIMENTS

The best mode for carrying out the invention is presented in terms of its preferred embodiment, herein depicted within the FIGS. 1 through 4e.

1. Detailed Description of the Figures

Figure 1:
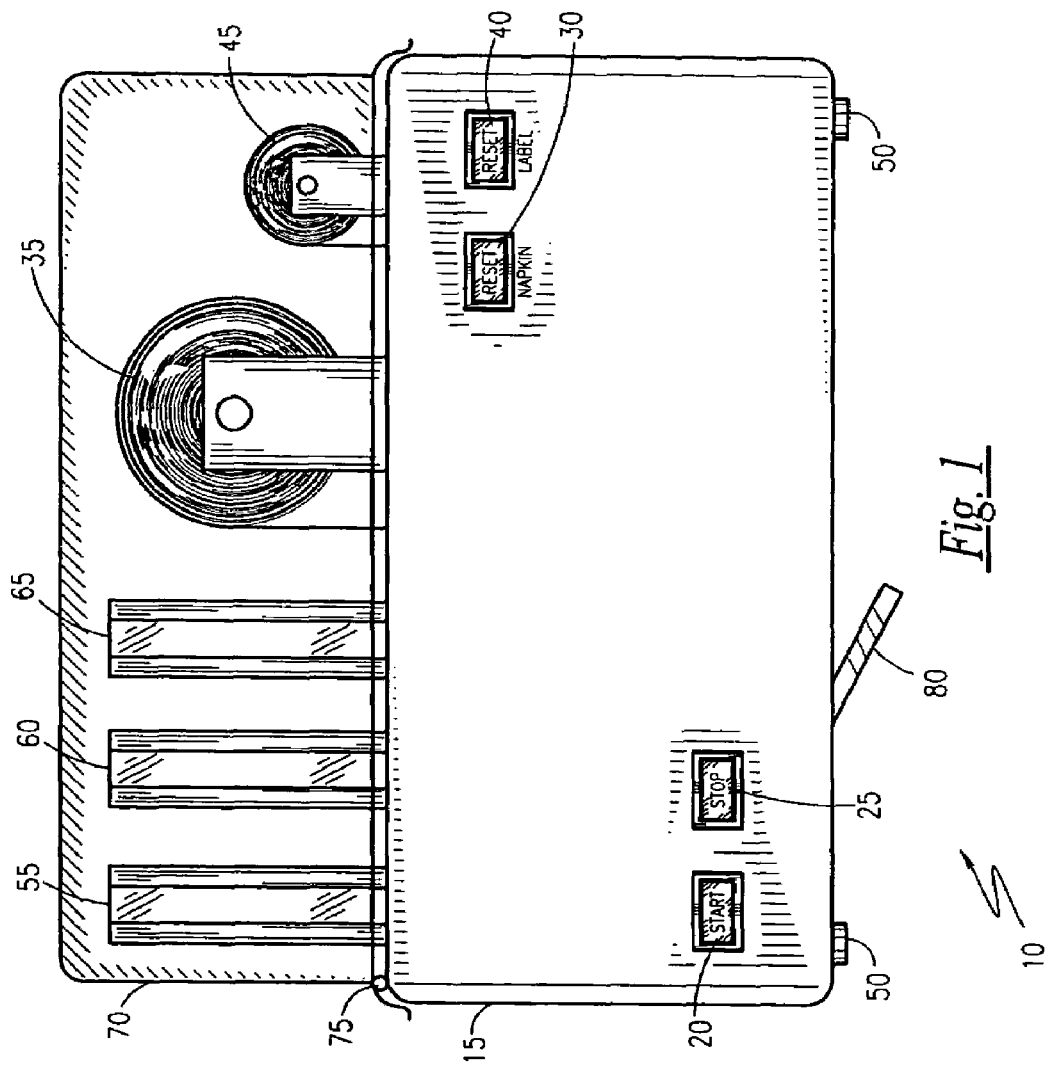
FIG. 1 is a front view of the automated flatware and napkin assembling apparatus 10, according to a preferred embodiment of the present invention.

Referring first to FIG. 1, a front view of the automated flatware and napkin assembling apparatus 10, according to a preferred embodiment of the present invention is shown. An automation enclosure 15 encloses the moving automatic components of the automated flatware and napkin assembling apparatus 10, thus protecting them from accidental contact and a possible safety hazard from the user. Controls mounted on the front of the automation enclosure 15 include a start switch 20 for activating the automated flatware and napkin assembling apparatus 10 and a stop switch 25 for a corresponding stopping function. A napkin reset switch 30 provides for the resetting of a roll of rolled paper napkins 35, such as after a jam or after a new roll of rolled paper napkins 35 is installed. Similarly, a label reset switch 40 provides for the resetting of a roll of rolled paper adhesive labels 45. The rolled paper napkins 35 is a pre-manufactured roll of paper napkins, similar in design to a roll of paper towels commonly found in a kitchen. The rolled paper adhesive labels 45 is a perforated roll of paper labels with pre-applied adhesive along one edge. A series of four mounting feet 50 (two of which are shown in this FIG. for sake of clarity), provide a suitable mounting base and prevent the automated flatware and napkin assembling apparatus 10 from moving along the horizontal surface such as a counter or table upon which it is set during operation. Also located on the top of the automation enclosure 15 is a spoon hopper 55, a fork hopper 60 and a knife hopper 65 that holds stacked silverware or flatware prior to wrapping. It is envisioned that the three hoppers along with the rolled paper napkins 35 and the rolled paper adhesive labels 45 have adequate capacity to wrap 50 bundles of flatware at one time prior to refilling. A cover 70, envisioned to be of a material type that blocks passage of ultraviolet radiation, provides protection against dust and dirt from contaminating the flatware contained in the spoon hopper 55, the fork hopper 60 and the knife hopper 65 as well as the rolled paper napkins 35 and the rolled paper adhesive labels 45. It also protects the operator or user from safety hazards, by requiring it to be in place prior to activation by the presence of a limit switch 75 which is wired to stop the process if the cover is removed. Said limit switch 75 also deactivates ultraviolet radiation sources, described in greater detail hereinbelow, as well as activates a cooling fan, not shown in this FIG., to remove excess heat generated by the ultraviolet radiation sources. Finally, an exit slot 80, on which the fully wrapped and secured flatware exits the automated flatware and napkin assembling apparatus 10 is provided at the bottom of the automation enclosure 15.

Figure 2:
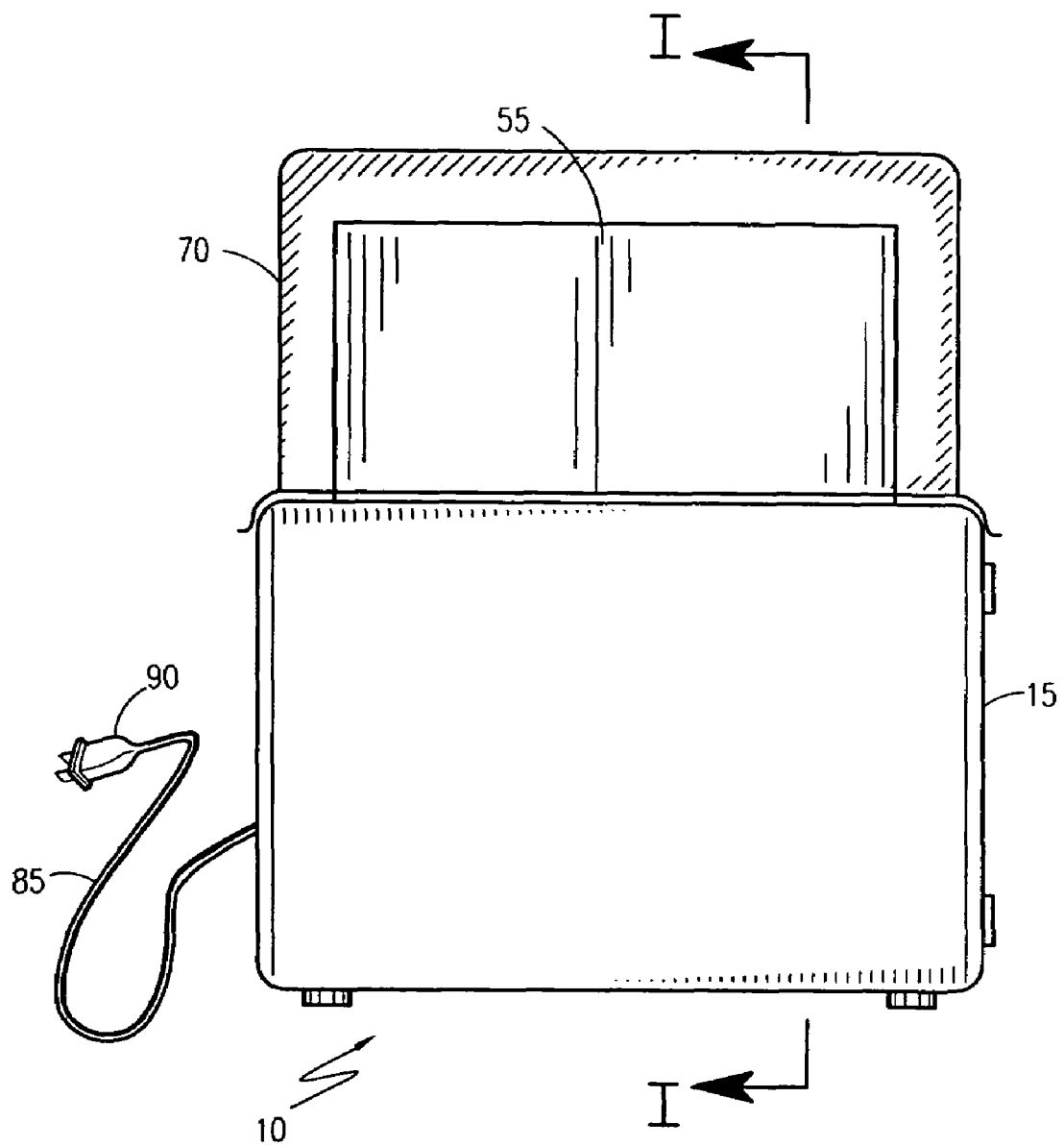
FIG. 2 is a side view of the automated flatware and napkin assembling apparatus 10.

Referring now to FIG. 2, a side view of the automated flatware and napkin assembling apparatus 10 is depicted. This FIG. more clearly details the cover 70 and how it completely encases the top of the automation enclosure 15 protecting it from dust and dirt. The spoon hopper 55 is visible in this view of the left side of the automation enclosure 15. Power for the automated flatware and napkin assembling apparatus 10 will be provided via a power cord 85 and a power plug 90 which will connect to commercially available AC power.

Figure 3:
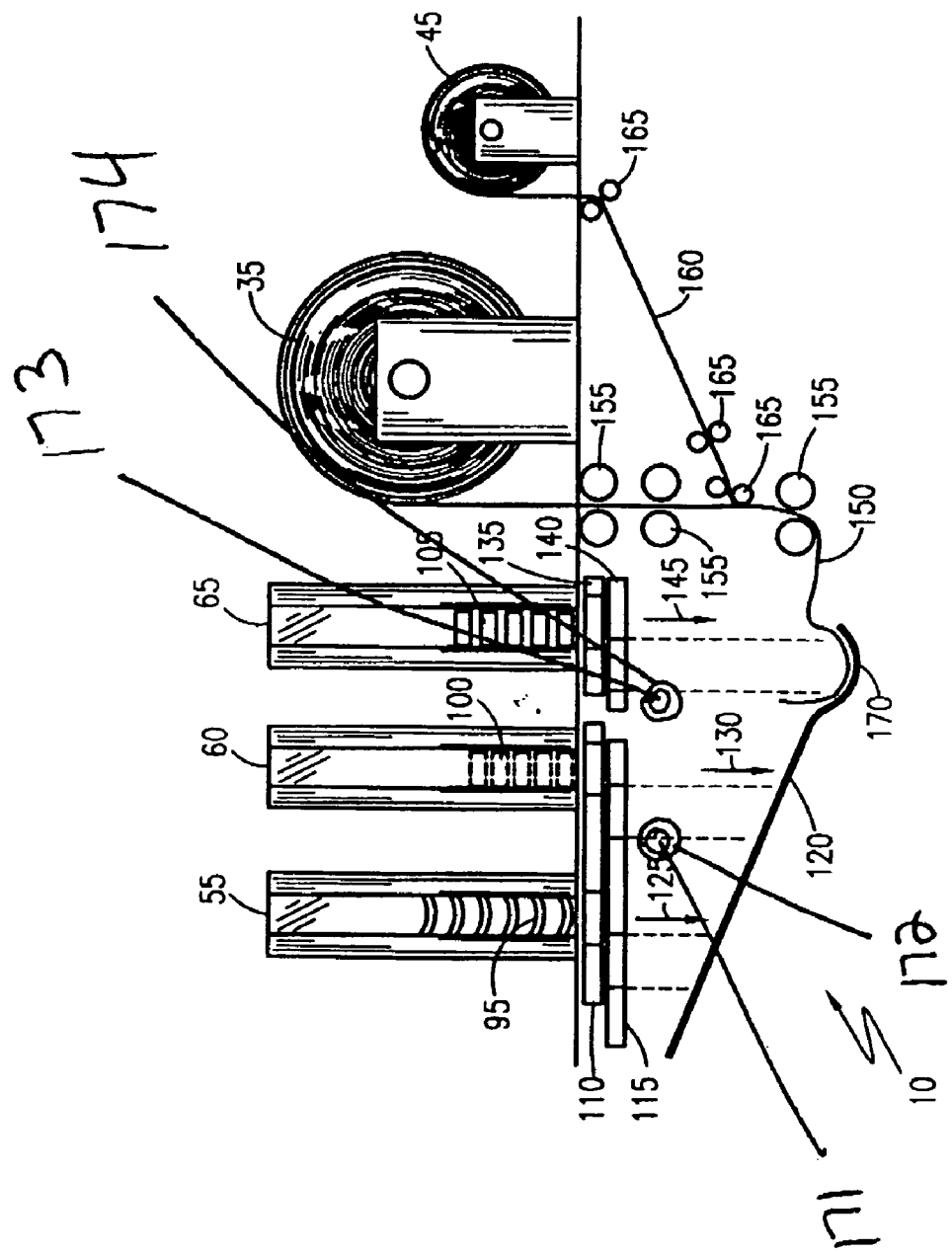
FIG. 3 is a sectional view of the automated flatware and napkin assembling apparatus 10 as seen along a line I-I as shown in FIG. 2.

Referring next to FIG. 3, an internal sectional view of the automated flatware and napkin assembling apparatus 10, as seen along a line I-I as seen in FIG. 2 is depicted. The spoon hopper 55, the fork hopper 60 and the knife hopper 65 are supplied and stocked with spoons 95, forks 100, and knives 105 respectively. A first upper indexing plate 110 working in conjunction with a first lower indexing plate 115, provides for the dropping of one spoon 95 and one fork 100 at a time on a sliding chute 120, as defined by a first travel path 125 and a second travel path 130. Similarly a second upper indexing plate 135 working in conjunction with a second lower indexing plate 140, provides for the dropping of one knife 105 at a time on the flatware trough 170, as defined by a third travel path 145. A napkin stream 150 is fed from the rolled paper napkins 35 by a series of first indexing rollers 155 working in a pinch roller arrangement. Similarly, a label stream 160 is fed from the rolled paper adhesive labels 45 by a series of second indexing rollers 165 working in a pinch roller arrangement. The first upper indexing plate 110, the first lower indexing plate 115 the second upper indexing plate 135, the second lower indexing plate 140, the first indexing rollers 155, the second indexing rollers 165 are all mechanically powered by a series of stepper motors. The stepper motors are activated by a logic controller such as Programmable Logic Controller (PLC) or a basic stamp module. The logic controller receives inputs from the start switch 20 (as shown in FIG. 1), the stop switch 25 (as shown in FIG. 1), the napkin reset switch 30 (as shown in FIG. 1), the rolled paper napkins 35 (as shown in FIG. 1) and a series of sensors such as proximity sensors, photoelectric eyes or the like. The logic controller, stepper motors, and sensors are well-known in the art, and can be designed, located, and programmed by those skilled in the art based upon this description of operation. The napkin stream 150 is routed into a flatware trough 170 located at the bottom of the sliding chute 120. Finally, a first ultraviolet lamp tube 171 is located is between hoppers 55 and 60, and underneath index plate 115, and a second ultraviolet lamp tube 173 is located between hoppers 60 and 65, and underneath index plate 140. Said first ultraviolet lamp tube 171 and second ultraviolet lamp tube 173 provide an ultraviolet radiation source which provides a second level of sanitization by using a Ultra-Violet radiation process on all silver ware, napkins, bands and surrounding internal working components. The first ultraviolet lamp tube 171 and second ultraviolet lamp tube 173 are surrounded by a first ultraviolet lamp tube shield 172 and a second ultraviolet lamp tube shield 174 respectively, to contain glass shards in case of accidental breakage. The practice of using ultraviolet radiation to reduce and/or eliminate microbiological contamination is well known in the art.

Figure 4A:
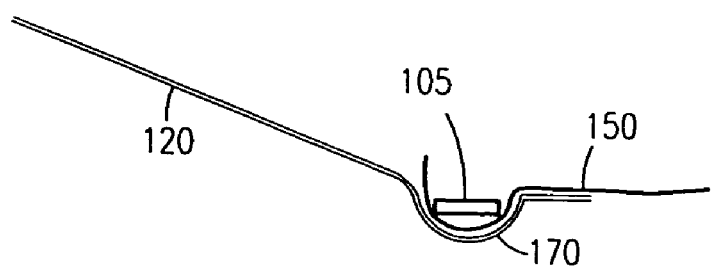
FIGS. 4a-4e are a series of sectional views as the flatware is assembled and wrapped as seen along the line I-I as shown in FIG. 1.
Figure 4B:
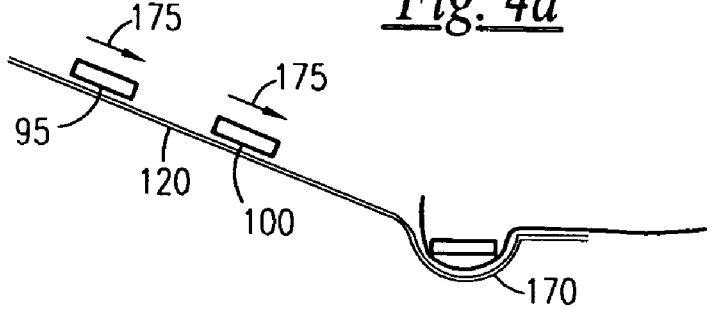
Figure 4C:
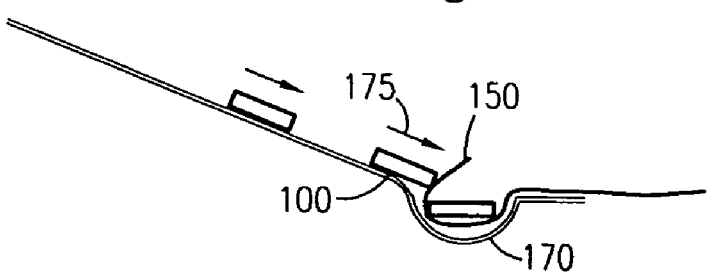
Figure 4D:
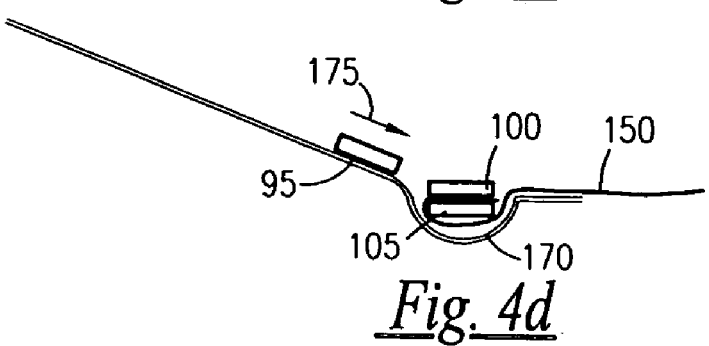
Figure 4E:
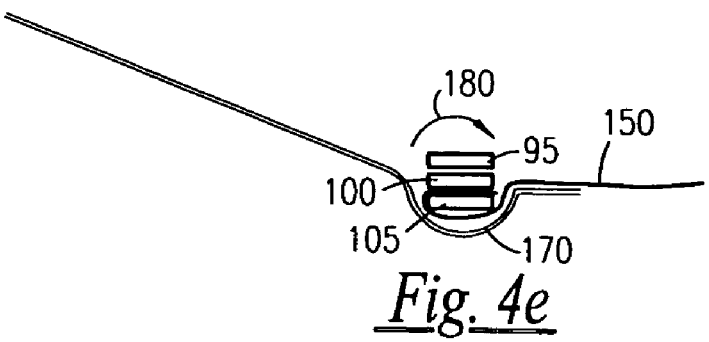

Referring finally to FIGS. 4a-4e, a series of sectional views of the actual flatware assembly process is depicted. The sectional views are also taken along a line I-I as seen in FIG. 2, and detail the area including and immediately adjacent to the flatware trough 170 as seen in FIG. 3. The sequence defined by these FIGS. define the operation of one cycle that occurs during one set of flatware assembly. In FIG. 4a, the condition immediately after the knife 105 has fallen upon the napkin stream 150 is depicted. The napkin stream 150, under the weight of the knife 105 has taken the shape of the flatware trough 170 at the end of the sliding chute 120. In FIG. 4b, the spoon 95 and the fork 100 have been dropped on the sliding chute 120 and are sliding toward the flatware trough 170 as defined by a fourth travel path 175. In FIG. 4c, the fork 100 has just contacted the leading edge of the napkin stream 150 and is proceeding to fold it over in the general momentum direction of the fourth travel path 175. In FIG. 4d, the fork 100 is in its final position in the flatware trough 170, and has pinched the napkin stream 150 against the knife 105. The spoon 95 is still continuing to slide down the sliding chute 120 as defined by the fourth travel path 175. Finally, in FIG. 4e, the knife 105, the fork 100, and the spoon 95 are in their final position in the flatware trough 170, with the napkin stream 150 firmly secured in between them. At this point, a series of automatically engaging jaws (not shown for clarity) grab the flatware bundle and rotate them in a direction defined by a rotational travel path 180 for multiple rotations. This action secures the flatware stack inside of the napkin stream 150. Additional actions secure the label stream 160 (as seen in FIG. 3) about the napkin stream 150 and the completed and secured bundle is ready for discharge through the exit slot 80 (as seen in FIG. 1)

In alternate embodiments, it is envisioned that the capacity for on-demand printing can be easily integrated into the present invention such as to eliminate the need for pre-printing of labels 45. As shown in FIG. 5, an ink jet printer head 190 is incorporated in line with the label stream 160 between the feed from the rolled paper adhesive labels 45 and the second indexing rollers 165. In such an arrangement, a print-on-demand capacity can be added within the label stream 160, with individual labels being printed as the label stream 160 is indexed passed the ink jet printer head 190. Similarly, as shown in FIG. 6 the ink jet printer head 190 can be incorporated in line with the napkin stream 150 between the feed from the rolled napkins 35 and the first indexing rollers 155.

In such an arrangement, a print-on-demand capacity can be added within the napkin stream 150, with individual advertising or communication messages being printed directly to the napkins 35 as the napkin stream 150 is indexed passed the ink jet printer head 190.

2. Operation of the Preferred Embodiment

The preferred embodiment of the present invention can be used by the common restaurant or cafeteria worker in a simple and effortless manner with minimal training. After acquisition of the automated flatware and napkin assembling apparatus 10, it is placed on a suitable horizontal surface such as a counter and table and connected to a source of electrical power using the power cord 85 and the power plug 90. Next, the spoon hopper 55, the fork hopper 60, and the knife hopper 65 are stocked with a suitable supply of spoons 95, forks 100 and knives 105, envisioned to be up to the quantity of 50 each. Finally, an adequate supply of rolled paper napkins 35 and rolled paper adhesive labels 45 is verified, the cover 70 is set into position, and the automated flatware and napkin assembling apparatus 10 is ready for use.

The automatic wrapping operation is begun by pressing the start switch 20. At this point in time, the first ultraviolet lamp tube 171 and second ultraviolet lamp tube 173 illuminate. Said illumination sterilizes the underside of all the flatware as they sit in the bottom of the flatware guides. As the flatware is dropped each passes by the first ultraviolet lamp tube 171 and second ultraviolet lamp tube 173, it is exposed on all sides to UV light energy. This ultraviolet energy is also applied to all interior components and supplies of the automated flatware and napkin assembling apparatus 10 including the rolled paper napkins 35 and the rolled paper adhesive labels 45, thereby killing all microbes and viruses either on the surface of the flatware or airborne inside the appliance. The internal mechanisms as defined in FIG. 3 and FIGS. 4a through 4e then allow for the wrapping of a set of flatware in a paper napkin and securing each set with an adhesive label. The completed set is then discharged via the exit slot 80. This process continues until all of the flatware contained in the automated flatware and napkin assembling apparatus 10 is wrapped, or the stop switch 25 is pressed.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. An automated flatware and napkin assembling apparatus comprising:
   a spoon hopper that holds stacked spoons prior to wrapping;
   a fork hopper that holds stacked forks prior to wrapping;
   a knife hopper that holds stacked knives prior to wrapping;
   rolled paper napkins;
   rolled paper labels, perforated, with adhesive along one edge;

an exit slot, on which the fully wrapped and secured flatware exits the automated flatware and napkin assembling apparatus is provided at the bottom of the automation enclosure;

first upper indexing plate working in conjunction with a first lower indexing plate for providing for the dropping of one spoon and one fork at a time on a sliding chute defined by a first travel path and a second travel path;

a second upper indexing plate working in conjunction with a second lower indexing plate for the dropping of one knife at a time into the flatware trough as defined by a third travel path;

a napkin stream fed from said rolled paper napkins by a series of first indexing rollers working in a pinch roller arrangement;

a label stream fed from the rolled paper adhesive by a series of second indexing rollers working in a pinch roller arrangement; and an ink jet printer head is incorporated in line with said label stream between the feed from said rolled paper labels and said second indexing rollers, said inkjet printer head is provided to print individual labels on each of said roll paper labels;

wherein said first upper indexing plate, said first lower indexing plate, said second upper indexing plate, said second lower indexing plate, said first indexing rollers, and said second indexing rollers are all mechanically powered by a series of stepper motors activated by a logic controller that receives inputs from a series of sensors to direct the napkin stream into a flatware trough located at the bottom of the sliding chute.

2. The automated flatware and napkin assembling apparatus of claim 1, further comprising a series of automatically engaging jaws for grabbing the flatware bundle and rotating it in a direction defined by a rotational travel path for multiple rotations such as to secures a flatware stack inside of said napkin stream.

3. The automated flatware and napkin assembling apparatus of claim 2, wherein said label stream is further secured about said napkin steam and the completed and secured bundle is ready for discharge through said exit slot.

4. The automated flatware and napkin assembly apparatus of claim 1, further comprising:

a first ultraviolet lamp tube positioned between said spoon hopper and said fork hopper and underneath said first lower indexing plate; and a second ultraviolet lamp tube positioned between said fork hopper and said knife hopper and underneath said second lower indexing plate, wherein said first and said second ultraviolet lamp tubes provide an ultraviolet radiation source to sanitize said spoons, said forks and said knifes.

5. The automated flatware and napkin assembly apparatus of claim 4, further comprising:

a first shield that surrounds said first ultraviolet lamp tube; and a second shield that surrounds said second ultraviolet lamp tube, wherein said first and said second shields contain any shattered shards in the case the glass on said lamps accidentally break.

6. An automated flatware and napkin assembling apparatus comprising:

spoon hopper that holds stacked spoons prior to wrapping;
a fork hopper that holds stacked forks prior to wrapping;
a knife hopper that holds stacked knives prior to wrapping;
rolled paper napkins;
rolled paper labels, perforated, with adhesive along one edge;

an exit slot, on which the fully wrapped and secured flatware exits the automated flatware and napkin assembling apparatus is provided at the bottom of the automation enclosure;

first upper indexing plate working in conjunction with a first lower indexing plate for providing for the dropping of one spoon and one fork at a time on a sliding chute defined by a first travel path and a second travel path;

a second upper indexing plate working in conjunction with a second lower indexing plate for the dropping of one knife at a time into the flatware trough as defined by a third travel path;

a napkin stream fed from said rolled paper napkins by a series of first indexing rollers working in a pinch roller arrangement;

an ink jet printer head is incorporated in line with said napkin stream between the feed from said rolled napkins and said first indexing rollers, said ink jet printer head is provided to print individual labels, advertisements and communications on each of said rolled paper napkins; and a label stream fed from the rolled paper adhesive labels by a series of second indexing rollers working in a pinch roller arrangement;

wherein said first upper indexing plate, said first lower indexing plate, said second upper indexing plate, said second lower indexing plate, said first indexing rollers, and said second indexing rollers are all mechanically powered by a series of stepper motors activated by a logic controller that receives inputs from a series of sensors to direct the napkin stream into a flatware trough located at the bottom of the sliding chute.

7. The automated flatware and napkin assembling apparatus of claim 6, further comprising a series of automatically engaging jaws for grabbing the flatware bundle and rotating it in a direction defined by a rotational travel path for multiple rotations such as to secures a flatware stack inside of said napkin stream.

8. The automated flatware and napkin assembling apparatus of claim 7, wherein said label stream is further secured about said napkin stream and the completed and secured bundle is ready for discharge through said exit slot.

9. The automated flatware and napkin assembly apparatus of claim 6, further comprising:

a first ultraviolet lamp tube positioned between said spoon hopper and said fork hopper and underneath said first lower indexing plate; and a second ultraviolet lamp tube positioned between said fork hopper and said knife hopper and underneath said second lower indexing plate, wherein said first and said second ultraviolet lamp tubes provide an ultraviolet radiation source to sanitize said spoons, said forks and said knifes.

10. The automated flatware and napkin assembly apparatus of claim 9, further comprising:

a first shield that surrounds said first ultraviolet lamp tube; and a second shield that surrounds said second ultraviolet lamp tube, wherein said first and said second shields contain any shattered shards in the case the glass on said lamps accidentally break.

* * * * *